US012667132B2

(12) United States Patent
Aoun et al.

(10) Patent No.: US 12,667,132 B2
(45) Date of Patent: Jun. 30, 2026

(54) CONSUMABLE FOR AEROSOL GENERATING APPARATUS

(71) Applicant: NICOVENTURES TRADING LIMITED, London (GB)

(72) Inventors: Walid Abi Aoun, London (GB); Gary Fallon, London (GB)

(73) Assignee: NICOVENTURES TRADING LIMITED, London (GB)

( * ) Notice: Subject to any disclaimer, the term of this patent is extended or adjusted under 35 U.S.C. 154(b) by 929 days.

(21) Appl. No.: 17/264,031

(22) PCT Filed: Jul. 31, 2019

(86) PCT No.: PCT/EP2019/070733
§ 371 (c)(1),
(2) Date: Jan. 28, 2021

(87) PCT Pub. No.: WO2020/025735
PCT Pub. Date: Feb. 6, 2020

(65) Prior Publication Data
US 2021/0161201 A1 Jun. 3, 2021

(30) Foreign Application Priority Data
Jul. 31, 2018 (GB) ..................................... 1812489

(51) Int. Cl.
*A24D 1/20* (2020.01)
*A24C 5/01* (2020.01)
*A24F 40/20* (2020.01)
*A24F 40/465* (2020.01)
(Continued)

(52) U.S. Cl.
CPC .................. *A24D 1/20* (2020.01); *A24C 5/01* (2020.01); *A24F 40/20* (2020.01); *A24F 40/465* (2020.01); *A61M 11/041* (2013.01); *H05B 6/108* (2013.01)

(58) Field of Classification Search
None
See application file for complete search history.

(56) References Cited

U.S. PATENT DOCUMENTS

| | | | |
|---|---|---|---|
| 5,105,831 A | 4/1992 | Banerjee et al. | |
| 5,613,505 A | 3/1997 | Campbell et al. | |
| 2005/0034723 A1 | 2/2005 | Bennett et al. | |

(Continued)

FOREIGN PATENT DOCUMENTS

| | | |
|---|---|---|
| CN | 103504479 | 1/2014 |
| CN | 103929988 A | 7/2014 |

(Continued)

OTHER PUBLICATIONS

"Decision of Refusal received for Japanese Patent Application No. 2021-505261, mailed on Jan. 31, 2023", 7 pages (4 pages English Translation and 3 pages of Official Copy).

(Continued)

*Primary Examiner* — Philip Y Louie
*Assistant Examiner* — Jeffrey A. Buckman
(74) *Attorney, Agent, or Firm* — Merchant & Gould P.C.

(57) ABSTRACT

Described herein is a consumable for use with apparatus for heating aerosolizable material to volatilise at least one component of the aerosolizable material. The consumable comprises a hollow tube comprising a carrier and aerosolizable material comprising an amorphous solid coated on the carrier.

19 Claims, 2 Drawing Sheets

(51) Int. Cl.
    *A61M 11/04*     (2006.01)
    *H05B 6/10*     (2006.01)

(56)       References Cited

U.S. PATENT DOCUMENTS

| | | | |
|---|---|---|---|
| 2006/0191546 A1* | 8/2006 | Takano | A24F 42/60 |
| | | | 131/270 |
| 2013/0037041 A1* | 2/2013 | Worm | A24F 40/50 |
| | | | 131/329 |
| 2015/0040929 A1 | 2/2015 | Hon | |
| 2016/0106154 A1 | 4/2016 | Lord | |
| 2016/0166564 A1 | 6/2016 | Myers et al. | |
| 2016/0309781 A1 | 10/2016 | Malgat et al. | |
| 2016/0354561 A1 | 12/2016 | McCullough | |
| 2017/0119049 A1 | 5/2017 | Blandino et al. | |
| 2017/0340014 A1* | 11/2017 | Batista | A24F 40/485 |
| 2018/0027884 A1* | 2/2018 | Zuber | A24F 40/42 |
| 2018/0042303 A1 | 2/2018 | Buehler | |

FOREIGN PATENT DOCUMENTS

| | | | |
|---|---|---|---|
| CN | 108024577 A | 5/2018 | |
| EP | 2246086 | 11/2010 | |
| JP | H08511175 A | 11/1996 | |
| JP | 2007259864 A | 10/2007 | |
| JP | 2014525237 A | 9/2014 | |
| JP | 2018504127 A | 2/2018 | |
| KR | 10-2018-0026666 | 3/2018 | |
| KR | 10-2018-0059921 | 6/2018 | |
| RU | 2604313 C2 | 12/2016 | |
| RU | 2637892 C1 | 12/2017 | |
| WO | WO2006022715 | 3/2006 | |
| WO | WO2013022936 | 2/2013 | |
| WO | WO-2013022936 A1 * | 2/2013 | A24F 40/10 |
| WO | 2016135224 A1 | 9/2016 | |
| WO | WO2016156509 | 10/2016 | |
| WO | WO2017005705 | 1/2017 | |
| WO | 2017068099 A1 | 4/2017 | |
| WO | 2017068101 A1 | 4/2017 | |
| WO | WO2017072147 | 5/2017 | |
| WO | 2018041924 A1 | 3/2018 | |
| WO | 2020025735 A1 | 2/2020 | |

OTHER PUBLICATIONS

"International Preliminary Report on Patentability received for PCT Patent Application No. PCT/EP2019/070733, mailed on Feb. 11, 2021", 8 pages.

"International Preliminary Report on Patentability received for PCT Patent Application No. PCT/EP2019/070735, mailed on Feb. 11, 2021", 7 pages.

"International Search Report and Written Opinion received for PCT Patent Application No. PCT/EP2019/070735, mailed on Nov. 14, 2019", 10 pages.

"Office Action received for Russian Patent Application No. 2021104722, mailed on Sep. 20, 2021", 5 pages.

"Reasons for Refusal received for Japanese Patent Application No. 2021-505261, mailed on Apr. 19, 2022", 10 pages (5 pages of English Translation and 5 pages of Official Copy).

"Reasons for Rejection received for Korean Patent Application No. 10-2021-7005925, mailed on Mar. 24, 2023", 16 pages (8 pages of English Translation and 8 pages of Official Copy).

"Search Report received for Chinese Patent Application No. 201980064759.7, mailed on Jan. 31, 2023", 3 pages (English Translation Only).

"Search Report received for Russian Patent Application No. 2021104722, mailed on Sep. 16, 2021", 2 pages. (Official Copy Only).

International Search Report and Written Opinion for International Application No. PCT/EP2019/070733 date mailed Nov. 14, 2019.

Korean Notice to File a Response for Korean Patent Application No. 10-2024-7013766, dated Jan. 26, 2026, 15 pages (8 pages English Translation, 7 pages Official Copy).

\* cited by examiner

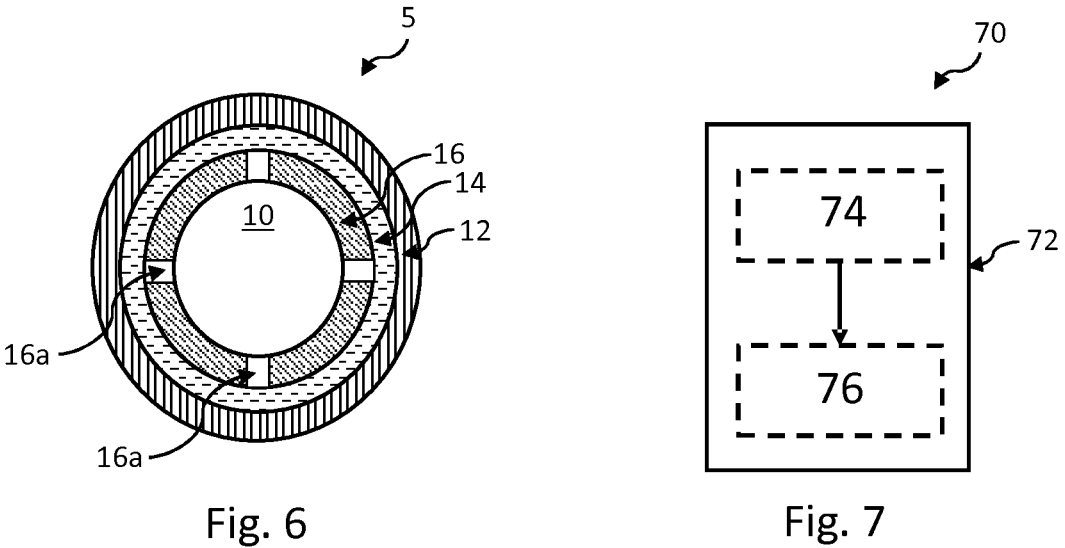
Fig. 6
Fig. 7
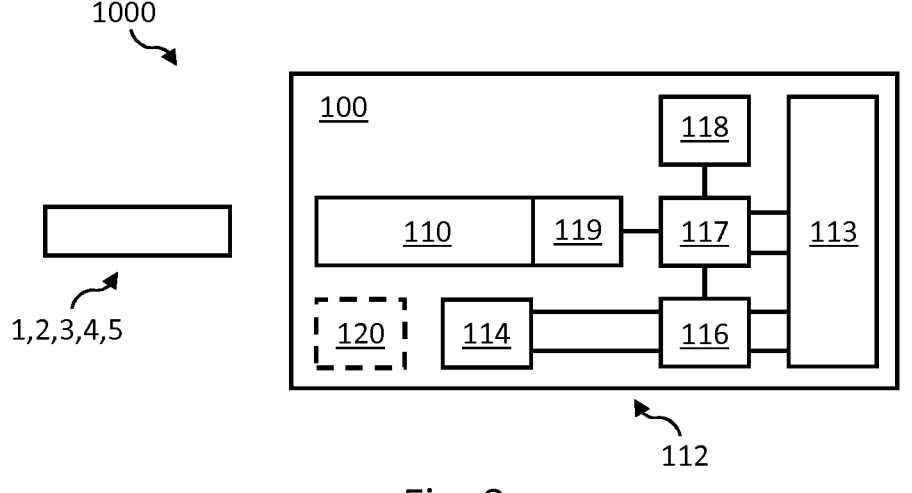
Fig. 8

CONSUMABLE FOR AEROSOL GENERATING APPARATUS

PRIORITY CLAIM

The present application is a National Phase entry of PCT Application No. PCT/EP2019/070733, filed Jul. 31, 2019 which claims priority from GB Patent Application No. 1812489.1 filed Jul. 31, 2018, each of which is hereby fully incorporated herein by reference.

TECHNICAL FIELD

The present disclosure relates to consumables for use with apparatus for heating aerosolizable material, methods of manufacturing consumables for use with apparatus for heating aerosolizable material, and systems comprising a consumable having aerosolizable material and an apparatus for heating the aerosolizable material of the consumable to volatilize at least one component of the aerosolizable material.

BACKGROUND

Smoking articles such as cigarettes, cigars and the like burn tobacco during use to create tobacco smoke. Attempts have been made to provide alternatives to these articles by creating products that release compounds without combusting. Examples of such products are so-called "heat not burn" products or tobacco heating devices or products, which release compounds by heating, but not burning, material. The material may be, for example, tobacco or other non-tobacco products, which may or may not contain nicotine.

SUMMARY

A first aspect of the present disclosure provides a consumable for use with apparatus for heating aerosolizable material to volatilize at least one component of the aerosolizable material, wherein the consumable comprises a hollow tube comprising a carrier and aerosolizable material comprising an amorphous solid coated on the carrier.

In an exemplary embodiment, the consumable is non-combustible.

In an exemplary embodiment, at least part of the aerosolizable material is located radially inwards of the carrier.

In an exemplary embodiment, the aerosolizable material forms at least part of a surface of the hollow tube. In an exemplary embodiment, the surface is an innermost surface of the hollow tube.

In an exemplary embodiment, the aerosolizable material forms at least a majority of the innermost surface of the hollow tube.

In an exemplary embodiment, the aerosolizable material forms all of the innermost surface of the hollow tube.

In an exemplary embodiment, at least part of the aerosolizable material is located radially outwards of the carrier.

In an exemplary embodiment, the aerosolizable material forms at least part of an outermost surface of the hollow tube.

A second aspect of the present disclosure provides a consumable for use with apparatus for heating aerosolizable material to volatilize at least one component of the aerosolizable material, wherein the consumable comprises a hollow tube comprising a carrier and aerosolizable material comprising an amorphous solid affixed to the carrier, and wherein the aerosolizable material forms at least part of an innermost surface of the hollow tube.

In an exemplary embodiment, the aerosolizable material forms at least a majority of the innermost surface of the hollow tube.

In an exemplary embodiment, the aerosolizable material forms all of the innermost surface of the hollow tube.

In an exemplary embodiment, the carrier is free from heating material that is heatable by penetration with a varying magnetic field.

In an exemplary embodiment, the consumable is free from heating material that is heatable by penetration with a varying magnetic field.

In an exemplary embodiment, the carrier is tubular.

In an exemplary embodiment, the carrier comprises a wound strip.

In an exemplary embodiment, the aerosolizable material is tubular.

In an exemplary embodiment, the consumable comprises heating material that is heatable by penetration with a varying magnetic field to thereby heat the aerosolizable material.

In an exemplary embodiment, the heating material comprises one or more materials selected from the group consisting of: an electrically-conductive material, a magnetic material, and a magnetic electrically-conductive material.

In an exemplary embodiment, the heating material comprises a metal or a metal alloy.

In an exemplary embodiment, the heating material comprises one or more materials selected from the group consisting of: aluminum, gold, iron, nickel, cobalt, conductive carbon, graphite, steel, plain-carbon steel, mild steel, stainless steel, ferritic stainless steel, molybdenum, silicon carbide, copper, and bronze.

In an exemplary embodiment, the carrier comprises the heating material.

In an exemplary embodiment, the carrier comprises a closed circuit of the heating material.

In an exemplary embodiment, the carrier consists of or substantially consists of the heating material.

In an exemplary embodiment, the heating material has a substantially constant cross-sectional area with axial distance along the consumable.

In an exemplary embodiment, the carrier comprises a first layer and a second layer, wherein the first layer comprises the heating material, wherein the second layer is not heatable by penetration with a varying magnetic field, and wherein the first layer is located between the aerosolizable material and the second layer.

In an exemplary embodiment, the second layer comprises one or more materials selected from the group consisting of: paper, card, paperboard, cardboard, reconstituted tobacco, and a plastics material.

In an exemplary embodiment, the carrier forms at least part of a surface of the consumable.

In an exemplary embodiment, the carrier forms at least a majority of the surface of the consumable.

In an exemplary embodiment, the carrier forms all of the surface of the consumable.

In an exemplary embodiment, the surface of the carrier is an outermost surface of the consumable.

In an exemplary embodiment, the surface of the carrier is an innermost surface of the consumable.

In an exemplary embodiment, the carrier has one or more holes extending therethrough for permitting aerosol generated from the aerosolizable material during heating of the aerosolizable material in use to pass to the surface of the consumable.

In an exemplary embodiment, the consumable comprises a body of porous aerosol containment material for containing aerosol generated from the aerosolizable material during heating of the aerosolizable material in use. In an exemplary embodiment, the aerosolizable material is located radially between the carrier and the body of porous aerosol containment material.

In an exemplary embodiment, the aerosolizable material has a thickness in a direction perpendicular to an axial direction of the consumable of between 0.1 millimeters and 5 millimeters.

A third aspect of the present disclosure provides a system for heating aerosolizable material to volatilize at least one component of the aerosolizable material, the system comprising: the consumable of the first aspect of the present disclosure or of the second aspect of the present disclosure; and apparatus for heating the aerosolizable material of the consumable to volatilize at least one component of the aerosolizable material, the apparatus comprising a heating zone for receiving the consumable, and a device for causing heating of the aerosolizable material when the consumable is in the heating zone.

In an exemplary embodiment, the device comprises a magnetic field generator for generating a varying magnetic field for penetrating the heating zone when the consumable is in the heating zone.

In an exemplary embodiment, the device comprises a heatable element comprising heating material, wherein the heatable element is in thermal contact with the heating zone, and wherein the device comprises a magnetic field generator for generating a varying magnetic field for penetrating the heatable element so as to cause heating of the heating zone.

In an exemplary embodiment, the device for causing heating of the aerosolizable material when the consumable is in the heating zone is configured for heating different sections of the heating zone independently of each other.

A fourth aspect of the present disclosure provides a method of manufacturing a consumable for use with apparatus for heating aerosolizable material to volatilize at least one component of the aerosolizable material, the method comprising: providing a hollow tube comprising a carrier and aerosolizable material comprising an amorphous solid affixed to the carrier.

In an exemplary embodiment, the providing comprises affixing the aerosolizable material to the carrier, and then forming the hollow tube.

In an exemplary embodiment, the affixing comprises coating the aerosolizable material onto the carrier.

In an exemplary embodiment, the coating comprises spraying or casting the aerosolizable material onto the carrier.

In an exemplary embodiment, the aerosolizable material forms at least part of an innermost surface of the hollow tube.

Further aspects of the present disclosure may provide the use of the consumable of the first or second aspect of the present disclosure in the generation of an inhalable aerosol.

BRIEF DESCRIPTION OF THE DRAWINGS

Embodiments of the disclosure will now be described, by way of example only, with reference to the accompanying drawings, in which:

FIG. 6 shows a schematic cross-sectional end view of an example of another consumable for use with apparatus for heating aerosolizable material to volatilize at least one component of the aerosolizable material;

FIG. 7 shows a flow diagram showing an example of a method of manufacturing a consumable for use with apparatus for heating aerosolizable material to volatilize at least one component of the aerosolizable material; and FIG. 8 shows a schematic view of an example of a system comprising a consumable and apparatus for heating aerosolizable material of the consumable to volatilize at least one component of the aerosolizable material.

DETAILED DESCRIPTION

Figures 1, 2, 3, 4, 5:
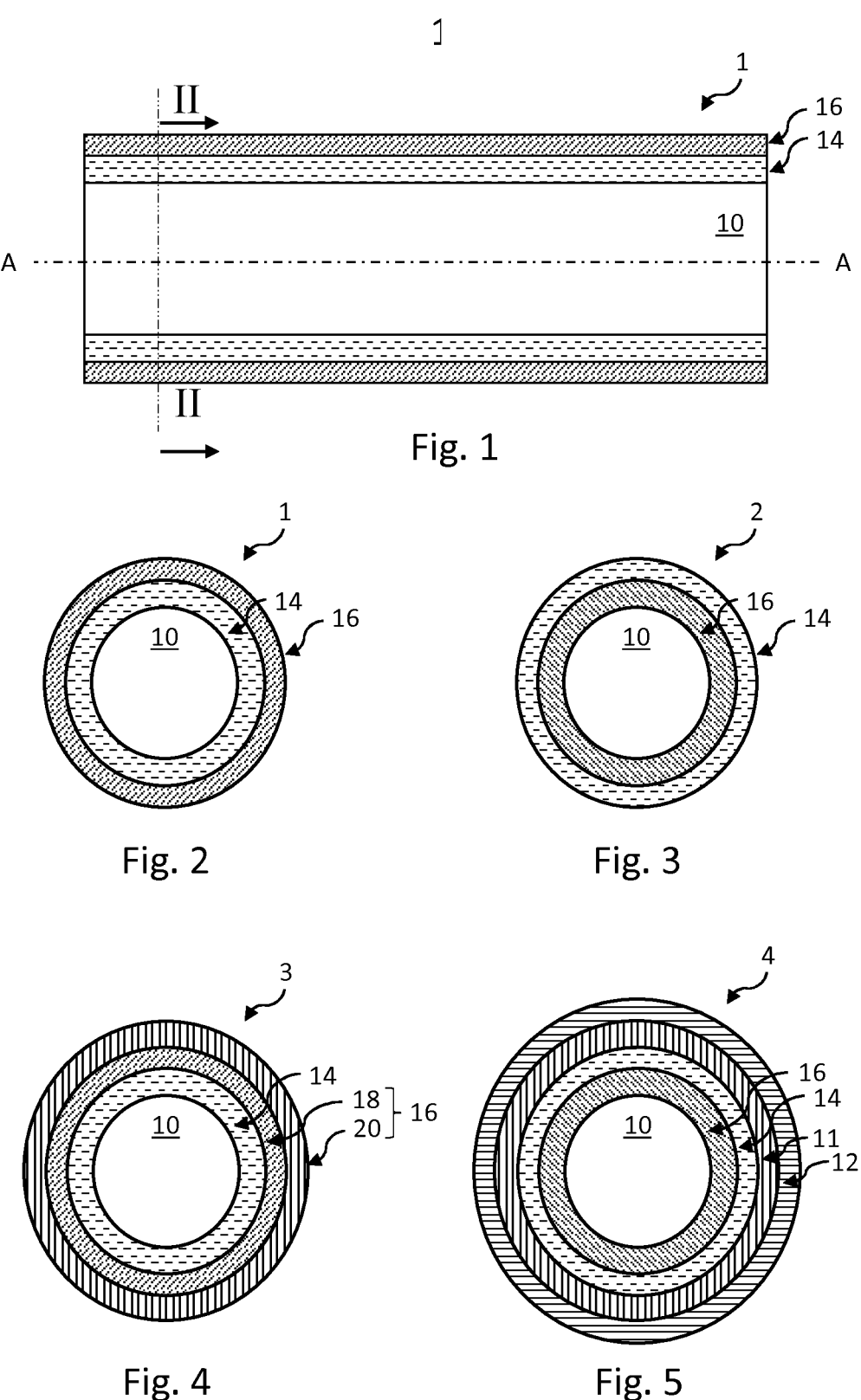
FIG. 1 shows a schematic cross-sectional side view of an example of a consumable for use with apparatus for heating aerosolizable material to volatilize at least one component of the aerosolizable material.
FIG. 2 shows a schematic cross-sectional end view of the consumable of FIG. 1.
FIG. 3 shows a schematic cross-sectional end view of an example of another consumable for use with apparatus for heating aerosolizable material to volatilize at least one component of the aerosolizable material.
FIG. 4 shows a schematic cross-sectional end view of an example of another consumable for use with apparatus for heating aerosolizable material to volatilize at least one component of the aerosolizable material.
FIG. 5 shows a schematic cross-sectional end view of an example of another consumable for use with apparatus for heating aerosolizable material to volatilize at least one component of the aerosolizable material.

As used herein, the term "aerosolizable material" includes materials that provide volatilized components upon heating, typically in the form of vapor or an aerosol. "Aerosolizable material" may be a non-tobacco-containing material or a tobacco-containing material. "Aerosolizable material" may, for example, include one or more of tobacco per se, tobacco derivatives, expanded tobacco, reconstituted tobacco, tobacco extract, homogenized tobacco or tobacco substitutes.

The aerosolizable material described herein comprises an "amorphous solid", which may alternatively be referred to as a "monolithic solid" (i.e. non-fibrous), or as a "dried gel". The amorphous solid is a solid material that may retain some fluid, such as liquid, within it. In some cases, the aerosolizable material comprises from about 50 wt %, 60 wt % or 70 wt % of amorphous solid, to about 90 wt %, 95 wt % or 100 wt % of amorphous solid. In some cases, the aerosolizable material consists of amorphous solid.

"Aerosolizable material" also may include other, non-tobacco, products, which, depending on the product, may or may not contain nicotine. "Aerosolizable material" may comprise one or more humectants, such as glycerol or propylene glycol.

The amorphous solid may be formed as a sheet. It may be incorporated into the consumable in sheet form. In some cases, the aerosolizable material may be included as a planar sheet, as a bunched or gathered sheet, as a crimped sheet, or as a rolled sheet (i.e. in the form of a tube). In some such cases, the amorphous solid of these embodiments may be included in a consumable or system as a sheet, such as a sheet circumscribing a rod of aerosolizable material (e.g. tobacco). In some other cases, the aerosolizable material may be formed as a sheet and then shredded and incorporated into the consumable. In some cases, the shredded sheet may be mixed with cut rag tobacco and incorporated into the consumable.

In some cases, the amorphous solid may comprise 1-60 wt % of a gelling agent wherein these weights are calculated on a dry weight basis.

Suitably, the amorphous solid may comprise from about 1 wt %, 5 wt %, 10 wt %, 15 wt %, 20 wt % or 25 wt % to about 60 wt %, 50 wt %, 45 wt %, 40 wt %, 35 wt %, 30 wt % or 27 wt % of a gelling agent (all calculated on a dry weight basis). For example, the amorphous solid may comprise 1-50 wt %, 5-40 wt %, 10-30 wt % or 15-27 wt % of a gelling agent.

In some embodiments, the gelling agent comprises a hydrocolloid. In some embodiments, the gelling agent comprises one or more compounds selected from the group comprising alginates, pectins, starches (and derivatives), celluloses (and derivatives), gums, silica or silicones compounds, clays, polyvinyl alcohol and combinations thereof. For example, in some embodiments, the gelling agent comprises one or more of alginates, pectins, hydroxyethyl cellulose, hydroxypropyl cellulose, carboxymethylcellulose, pullulan, xanthan gum guar gum, carrageenan, agarose, acacia gum, fumed silica, PDMS, sodium silicate, kaolin and polyvinyl alcohol. In some cases, the gelling agent comprises alginate and/or pectin, and may be combined with a setting agent (such as a calcium source) during formation of the amorphous solid. In some cases, the amorphous solid may comprise a calcium-crosslinked alginate and/or a calcium-crosslinked pectin.

In some embodiments, the gelling agent comprises alginate, and the alginate is present in the amorphous solid in an amount of from 10-30 wt % of the amorphous solid (calculated on a dry weight basis). In some embodiments, alginate is the only gelling agent present in the amorphous solid. In other embodiments, the gelling agent comprises alginate and at least one further gelling agent, such as pectin.

In some embodiments the amorphous solid may include gelling agent comprising carrageenan.

Suitably, the amorphous solid may comprise from about 5 wt %, 10 wt %, 15 wt %, or 20 wt % to about 80 wt %, 70 wt %, 60 wt %, 55 wt %, 50 wt %, 45 wt % 40 wt %, or 35 wt % of an aerosol generating agent (all calculated on a dry weight basis). The aerosol generating agent may act as a plasticizer. For example, the amorphous solid may comprise 10-60 wt %, 15-50 wt % or 20-40 wt % of an aerosol generating agent. In some cases, the aerosol generating agent comprises one or more compound selected from erythritol, propylene glycol, glycerol, triacetin, sorbitol and xylitol. In some cases, the aerosol generating agent comprises, consists essentially of or consists of glycerol. The inventors have established that if the content of the plasticizer is too high, the amorphous solid may absorb water resulting in a material that does not create an appropriate consumption experience in use. The inventors have established that if the plasticizer content is too low, the amorphous solid may be brittle and easily broken. The plasticizer content specified herein provides an amorphous solid flexibility which allows the amorphous solid sheet to be wound onto a bobbin, which is useful in manufacture of aerosol generating articles.

In some cases, the amorphous solid may comprise a flavor. Suitably, the amorphous solid may comprise up to about 60 wt %, 50 wt %, 40 wt %, 30 wt %, 20 wt %, 10 wt % or 5 wt % of a flavor. In some cases, the amorphous solid may comprise at least about 0.1 wt %, 0.5 wt %, 1 wt %, 2 wt %, 5 wt % 10 wt %, 20 wt % or 30 wt % of a flavor (all calculated on a dry weight basis). For example, the amorphous solid may comprise 0.1-60 wt %, 1-60 wt %, 5-60 wt %, 10-60 wt %, 20-50 wt % or 30-40 wt % of a flavor. In some cases, the flavor (if present) comprises, consists essentially of or consists of menthol. In some cases, the amorphous solid does not comprise a flavor.

In some cases, the amorphous solid comprises an active substance. For example, in some cases, the amorphous solid comprises a tobacco material and/or nicotine. For example, the amorphous solid may comprise powdered tobacco and/or nicotine and/or a tobacco extract. In some cases, the amorphous solid may comprise from about 1 wt %, 5 wt %, 10 wt %, 15 wt %, 20 wt % or 25 wt % to about 70 wt %, 50 wt %, 45 wt % or 40 wt % (calculated on a dry weight basis) of active substance. In some cases, the amorphous solid may comprise from about 1 wt %, 5 wt %, 10 wt %, 15 wt %, 20 wt % or 25 wt % to about 70 wt %, 60 wt %, 50 wt %, 45 wt % or 40 wt % (calculated on a dry weight basis) of a tobacco material and/or nicotine.

In some cases, the amorphous solid comprises an active substance such as tobacco extract. In some cases, the amorphous solid may comprise 5-60 wt % (calculated on a dry weight basis) of tobacco extract. In some cases, the amorphous solid may comprise from about 5 wt %, 10 wt %, 15 wt %, 20 wt % or 25 wt % to about 55 wt %, 50 wt %, 45 wt % or 40 wt % (calculated on a dry weight basis) tobacco extract. For example, the amorphous solid may comprise 5-60 wt %, 10-55 wt % or 25-55 wt % of tobacco extract. The tobacco extract may contain nicotine at a concentration such that the amorphous solid comprises 1 wt % 1.5 wt %, 2 wt % or 2.5 wt % to about 6 wt %, 5 wt %, 4.5 wt % or 4 wt % (calculated on a dry weight basis) of nicotine. In some cases, there may be no nicotine in the amorphous solid other than that which results from the tobacco extract.

In some embodiments the amorphous solid comprises no tobacco material but does comprise nicotine. In some such cases, the amorphous solid may comprise from about 1 wt %, 2 wt %, 3 wt % or 4 wt % to about 20 wt %, 15 wt %, 10 wt % or 5 wt % (calculated on a dry weight basis) of nicotine. For example, the amorphous solid may comprise 1-20 wt % or 2-5 wt % of nicotine.

In some cases, the total content of active substance and/or flavor may be at least about 0.1 wt %, 1 wt %, 5 wt %, 10 wt %, 20 wt %, 25 wt % or 30 wt %. In some cases, the total content of active substance and/or flavor may be less than about 80 wt %, 70 wt %, 60 wt %, 50 wt % or 40 wt % (all calculated on a dry weight basis).

In some cases, the total content of tobacco material, nicotine and flavor may be at least about 1 wt %, 5 wt %, 10 wt %, 20 wt %, 25 wt % or 30 wt %. In some cases, the total content of tobacco material, nicotine and flavor may be less than about 80 wt %, 70 wt %, 60 wt %, 50 wt % or 40 wt % (all calculated on a dry weight basis).

In some cases, the amorphous solid comprises from about 1 wt % to about 15 wt % water, or from about 5 wt % to about 15 wt % calculated on a wet weight basis. Suitably, the water content of the amorphous solid may be from about 5 wt %, 7 wt % or 9 wt % to about 15 wt %, 13 wt % or 11 wt % (WWB), most suitably about 10 wt %.

In some embodiments, the amorphous solid is a hydrogel and comprises less than about 20 wt % of water calculated on a wet weight basis. In some cases, the hydrogel may comprise less than about 15 wt %, 12 wt % or 10 wt % of water calculated on a wet weight basis (WWB). In some cases, the hydrogel may comprise at least about 2 wt % or at least about 5 wt % of water (WWB).

The amorphous solid may be made from a gel, and this gel may additionally comprise a solvent, included at 0.1-50 wt %. However, the inventors have established that the inclusion of a solvent in which the flavor is soluble may reduce the gel stability and the flavor may crystallize out of the gel. As such, in some cases, the gel does not include a solvent in which the flavor is soluble.

In some embodiments, the amorphous solid comprises less than 60 wt % of a filler, such as from 1 wt % to 60 wt %, or 5 wt % to 50 wt %, or 5 wt % to 30 wt %, or 10 wt % to 20 wt %.

In other embodiments, the amorphous solid comprises less than 20 wt %, suitably less than 10 wt % or less than 5 wt % of a filler. In some cases, the amorphous solid comprises less than 1 wt % of a filler, and in some cases, comprises no filler.

The filler, if present, may comprise one or more inorganic filler materials, such as calcium carbonate, perlite, vermiculite, diatomaceous earth, colloidal silica, magnesium oxide, magnesium sulphate, magnesium carbonate, and suitable inorganic sorbents, such as molecular sieves. The filler may comprise one or more organic filler materials such as wood pulp, cellulose and cellulose derivatives. In particular cases, the amorphous solid comprises no calcium carbonate such as chalk.

In particular embodiments which include filler, the filler is fibrous. For example, the filler may be a fibrous organic filler material such as wood pulp, hemp fiber, cellulose or cellulose derivatives. Without wishing to be bound by theory, it is believed that including fibrous filler in an amorphous solid may increase the tensile strength of the material. This may be particularly advantageous in examples wherein the amorphous solid is provided as a sheet, such as when an amorphous solid sheet circumscribes a rod of aerosolizable material.

In some embodiments, the amorphous solid does not comprise tobacco fibers. In particular embodiments, the amorphous solid does not comprise fibrous material.

In some embodiments, the aerosol generating material does not comprise tobacco fibers. In particular embodiments, the aerosol generating material does not comprise fibrous material.

In some embodiments, the aerosol generating substrate does not comprise tobacco fibers. In particular embodiments, the aerosol generating substrate does not comprise fibrous material.

In some embodiments, the consumable does not comprise tobacco fibers. In particular embodiments, the consumable does not comprise fibrous material.

In some cases, the amorphous solid may consist essentially of, or consist of a gelling agent, an aerosol generating agent, a tobacco material and/or a nicotine source, water, and optionally a flavor.

A method of making an aerosolizable material may comprise (a) forming a slurry comprising components of the amorphous solid or precursors thereof, (b) forming a layer of the slurry, and (c) setting the slurry to form a gel and (d) drying to form an amorphous solid.

The step (b) of forming a layer of the slurry may comprise spraying, casting or extruding the slurry, for example. In some cases, the layer is formed by electro-spraying the slurry. In some cases, the layer is formed by casting the slurry.

In some cases, the slurry is applied to a carrier.

In some cases, the steps (b) and/or (c) and/or (d) may, at least partially, occur simultaneously (for example, during electro-spraying). In some cases, these steps may occur sequentially.

The step (c) of setting the gel may comprise the addition of a setting agent to the slurry. For example, the slurry may comprise sodium, potassium or ammonium alginate as a gel-precursor, and a setting agent comprising a calcium source (such as calcium chloride), may be added to the slurry to form a calcium alginate gel.

The total amount of the setting agent, such as a calcium source, may be 0.5-5 wt % (calculated on a dry weight basis). The inventors have found that the addition of too little setting agent may result in an amorphous solid which does not stabilize the amorphous solid components and results in these components dropping out of the amorphous solid. The inventors have found that the addition of too much setting agent results in an amorphous solid that is very tacky and consequently has poor handleability.

Alginate salts are derivatives of alginic acid and are typically high molecular weight polymers (10-600 kDa). Alginic acid is a copolymer of β-D-mannuronic (M) and α-L-guluronic acid (G) units (blocks) linked together with (1,4)-glycosidic bonds to form a polysaccharide. On addition of calcium cations, the alginate crosslinks to form a gel. The inventors have determined that alginate salts with a high G monomer content more readily form a gel on addition of the calcium source. In some cases therefore, the gel-precursor pay comprise an alginate salt in which at least about 40%, 45%, 50%, 55%, 60% or 70% of the monomer units in the alginate copolymer are α-L-guluronic acid (G) units.

The drying step may cause the cast material thickness to reduce by at least 80%, suitably 85% or 87%. For instance, the slurry may be cast at a thickness of 2 mm, and the resulting dried amorphous solid material may have a thickness of 0.2 mm.

In some cases, the amorphous solid may have a thickness of about 0.015 mm to about 1.0 mm. Suitably, the thickness may be in the range of about 0.05 mm, 0.1 mm or 0.15 mm to about 0.5 mm or 0.3 mm. The inventors have found that a material having a thickness of 0.2 mm is particularly suitable. The amorphous solid may comprise more than one layer, and the thickness described herein refers to the aggregate thickness of those layers.

In some cases, the slurry solvent may consist essentially of or consist of water. In some cases, the slurry may comprise from about 50 wt %, 60 wt %, 70 wt %, 80 wt % or 90 wt % of solvent (WWB).

In cases where the solvent consists of water, the dry weight content of the slurry may match the dry weight content of the amorphous solid. Thus, the discussion herein relating to the solid composition is explicitly disclosed in combination with the slurry aspect of the disclosure.

In some examples, the slurry has a viscosity of from about 10 to about 20 Pa·s at 46.5° C., such as from about 14 to about 16 Pa·s at 46.5° C.

The aerosolizable material comprising the amorphous solid may have any suitable area density, such as from 30 $g/m^2$ to 120 $g/m^2$. In some embodiments, aerosolizable material may have an area density of from about 30 to 70 $g/m^2$, or about 40 to 60 $g/m^2$. In some embodiments, the amorphous solid may have an area density of from about 80 to 120 $g/m^2$, or from about 70 to 110 $g/m^2$, or particularly from about 90 to 110 $g/m^2$. Such area densities may be particularly suitable where the aerosol-generating material is included in a consumable or system in sheet form, or as a shredded sheet (described further hereinbelow).

In some examples, the amorphous solid in sheet form may have a tensile strength of from around 200 N/m to around 900 N/m. In some examples, such as where the amorphous solid does not comprise a filler, the amorphous solid may have a tensile strength of from 200 N/m to 400 N/m, or 200 N/m to 300 N/m, or about 250 N/m. Such tensile strengths may be particularly suitable for embodiments wherein the aerosolizable material is formed as a sheet and then shredded and incorporated into a consumable. In some examples, such as where the amorphous solid comprises a filler, the amorphous solid may have a tensile strength of from 600 N/m to 900 N/m, or from 700 N/m to 900 N/m, or around 800 N/m. Such tensile strengths may be particularly suitable for embodiments wherein the aerosolizable material is included in a consumable or system as a rolled sheet, suitably in the form of a tube In one particular case, the carrier may be a paper-backed foil; the paper layer abuts the amorphous solid layer and the properties discussed in the previous paragraphs are afforded by this abutment. The foil backing is substantially impermeable, providing control of the aerosol flow path. A metal foil backing may also serve to conduct heat to the amorphous solid.

In another case, the foil layer of the paper-backed foil abuts the amorphous solid. The foil is substantially impermeable, thereby preventing water provided in the amorphous solid to be absorbed into the paper which could weaken its structural integrity.

In some cases, the carrier is formed from or comprises metal foil, such as aluminum foil. A metallic carrier may allow for better conduction of thermal energy to the amorphous solid. Additionally, or alternatively, a metal foil may function as a susceptor in an induction heating system. In particular embodiments, the carrier comprises a metal foil layer and a support layer, such as cardboard. In these embodiments, the metal foil layer may have a thickness of less than 20 $\mu m$, such as from about 1 $\mu m$ to about 10 $\mu m$, suitably about 5 $\mu m$.

The active substance as used herein may be a physiologically active material, which is a material intended to achieve or enhance a physiological response. The active substance may for example be selected from nutraceuticals, nootropics, and psychoactives. The active substance may be naturally occurring or synthetically obtained. The active substance may comprise for example nicotine, caffeine, taurine, theine, vitamins such as B6 or B12 or C, melatonin, cannabinoids, or constituents, derivatives, or combinations thereof. The active substance may comprise one or more constituents, derivatives or extracts of tobacco, cannabis or another botanical.

In some embodiments, the active substance comprises nicotine.

In some embodiments, the active substance comprises caffeine, melatonin or vitamin B12.

As noted herein, the active substance may comprise one or more constituents, derivatives or extracts of cannabis, such as one or more cannabinoids or terpenes.

Cannabinoids are a class of natural or synthetic chemical compounds which act on cannabinoid receptors (i.e., CB1 and CB2) in cells that repress neurotransmitter release in the brain. Cannabinoids may be naturally occurring (phytocannabinoids) from plants such as cannabis, from animals (endocannabinoids), or artificially manufactured (synthetic cannabinoids). Cannabis species express at least 85 different phytocannabinoids, and are divided into subclasses, including cannabigerols, cannabichromenes, cannabidiols, tetrahydrocannabinols, cannabinols and cannabinodiols, and other cannabinoids. Cannabinoids found in cannabis include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), and tetrahydrocannabivarinic acid (THCV A).

As noted herein, the active substance may comprise or be derived from one or more botanicals or constituents, derivatives or extracts thereof. As used herein, the term "botanical" includes any material derived from plants including, but not limited to, extracts, leaves, bark, fibers, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha arvensis, Mentha* c.v., *Mentha niliaca, Mentha piperita, Mentha piperita citrata* c.v., *Mentha piperita* c.v., *Mentha spicata crispa, Mentha cordifolia, Mentha longifolia, Mentha suaveolens variegata, Mentha pulegium, Mentha spicata* c.v. and *Mentha suaveolens*.

In some embodiments, the botanical is selected from eucalyptus, star anise, cocoa and hemp.

In some embodiments, the botanical is selected from rooibos and fennel.

As used herein, the terms "flavor" and "flavorant" refer to materials which, where local regulations permit, may be used to create a desired taste, aroma or other somatosensorial sensation in a product for adult consumers.

They may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

The flavor may suitably comprise one or more mint-flavors suitably a mint oil from any species of the genus *Mentha*. The flavor may suitably comprise, consist essentially of or consist of menthol.

In some embodiments, the flavor comprises menthol, spearmint and/or peppermint.

In some embodiments, the flavor comprises flavor components of cucumber, blueberry, citrus fruits and/or redberry.

In some embodiments, the flavor comprises eugenol.

In some embodiments, the flavor comprises flavor components extracted from tobacco.

In some embodiments, the flavor comprises flavor components extracted from cannabis.

In some embodiments, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucalyptol, WS-3.

As used herein, the term "aerosol generating agent" refers to an agent that promotes the generation of an aerosol. An aerosol generating agent may promote the generation of an aerosol by promoting an initial vaporization and/or condensation of a gas to an inhalable solid and/or liquid aerosol.

Suitable aerosol generating agents include, but are not limited to: a polyol such as erythritol, sorbitol, glycerol, and glycols like propylene glycol or triethylene glycol; a non-polyol such as monohydric alcohols, high boiling point hydrocarbons, acids such as lactic acid, glycerol derivatives, esters such as diacetin, triacetin, triethylene glycol diacetate, triethyl citrate or myristates including ethyl myristate and isopropyl myristate and aliphatic carboxylic acid esters such as methyl stearate, dimethyl dodecanedioate and dimethyl tetradecanedioate. The aerosol generating agent may suitably have a composition that does not dissolve menthol. The aerosol generating agent may suitably comprise, consist essentially of or consist of glycerol.

As used herein, the term "tobacco material" refers to any material comprising tobacco or derivatives therefore. The term "tobacco material" may include one or more of tobacco, tobacco derivatives, expanded tobacco, reconstituted tobacco or tobacco substitutes. The tobacco material may comprise one or more of ground tobacco, tobacco fiber, cut tobacco, extruded tobacco, tobacco stem, reconstituted tobacco and/or tobacco extract.

The tobacco used to produce tobacco material may be any suitable tobacco, such as single grades or blends, cut rag or whole leaf, including Virginia and/or Burley and/or Oriental. It may also be tobacco particle 'fines' or dust, expanded tobacco, stems, expanded stems, and other processed stem materials, such as cut rolled stems. The tobacco material may be a ground tobacco or a reconstituted tobacco material. The reconstituted tobacco material may comprise tobacco fibers, and may be formed by casting, a Fourdrinier-based paper making-type approach with back addition of tobacco extract, or by extrusion.

In some embodiments, the amorphous solid comprises menthol.

Particular embodiments comprising a menthol-containing amorphous solid may be particularly suitable for including in a consumable or system as a shredded sheet. In these embodiments, the amorphous solid may have the following composition (DWB): gelling agent (preferably comprising alginate, more preferably comprising a combination of alginate and pectin) in an amount of from about 20 wt % to about 40 wt %, or about 25 wt % to 35 wt %; menthol in an amount of from about 35 wt % to about 60 wt %, or from about 40 wt % to 55 wt %; aerosol generating agent (preferably comprising glycerol) in an amount of from about 10 wt % to about 30 wt %, or from about 15 wt % to about 25 wt % (DWB).

In one embodiment, the amorphous solid comprises about 32-33 wt % of an alginate/pectin gelling agent blend; about 47-48 wt % menthol flavorant; and about 19-20 wt % glycerol aerosol generating agent (DWB).

As noted above, the amorphous solid of these embodiments may be included in a consumable or system as a shredded sheet. The shredded sheet may be provided in the consumable or system blended with cut tobacco. Alternatively, the amorphous solid may be provided as a non-shredded sheet. Suitably, the shredded or non-shredded sheet has a thickness of from about 0.015 mm to about 1 mm, preferably from about 0.02 mm to about 0.07 mm.

Particular embodiments of the menthol-containing amorphous solid may be particularly suitable for including in a consumable or system as a sheet, such as a sheet circumscribing a rod of aerosolizable material (e.g. tobacco). In these embodiments, the amorphous solid may have the following composition (DWB): gelling agent (preferably comprising alginate, more preferably comprising a combination of alginate and pectin) in an amount of from about 5 wt % to about 40 wt %, or about 10 wt % to 30 wt %; menthol in an amount of from about 10 wt % to about 50 wt %, or from about 15 wt % to 40 wt %; aerosol generating agent (preferably comprising glycerol) in an amount of from about 5 wt % to about 40 wt %, or from about 10 wt % to about 35 wt %; and optionally filler in an amount of up to 60 wt %—for example, in an amount of from 5 wt % to 20 wt %, or from about 40 wt % to 60 wt % (DWB).

In one of these embodiments, the amorphous solid comprises about 11 wt % of an alginate/pectin gelling agent blend, about 56 wt % woodpulp filler, about 18% menthol flavorant and about 15 wt % glycerol (DWB).

In another of these embodiments, the amorphous solid comprises about 22 wt % of an alginate/pectin gelling agent blend, about 12 wt % woodpulp filler, about 36% menthol flavorant and about 30 wt % glycerol (DWB).

As noted above, the amorphous solid of these embodiments may be included as a sheet. In one embodiment, the sheet is provided on a carrier comprising paper. In one embodiment, the sheet is provided on a carrier comprising metal foil, suitably aluminum metal foil. In this embodiment, the amorphous solid may abut the metal foil.

In one embodiment, the sheet forms part of a laminate material with a layer (preferably comprising paper) attached to a top and bottom surface of the sheet. Suitably, the sheet of amorphous solid has a thickness of from about 0.015 mm to about 1 mm.

In some embodiments, the amorphous solid comprises a flavorant which does not comprise menthol. In these embodiments, the amorphous solid may have the following composition (DWB): gelling agent (preferably comprising alginate) in an amount of from about 5 to about 40 wt %, or from about 10 wt % to about 35 wt %, or from about 20 wt % to about 35 wt %; flavorant in an amount of from about 0.1 wt % to about 40 wt %, of from about 1 wt % to about 30 wt %, or from about 1 wt % to about 20 wt %, or from about 5 wt % to about 20 wt %; aerosol generating agent (preferably comprising glycerol) in an amount of from 15 wt % to 75 wt %, or from about 30 wt % to about 70 wt %, or from about 50 wt % to about 65 wt %; and optionally filler (suitably woodpulp) in an amount of less than about 60 wt %, or about 20 wt %, or about 10 wt %, or about 5 wt % (preferably the amorphous solid does not comprise filler) (DWB).

In one of these embodiments, the amorphous solid comprises about 27 wt % alginate gelling agent, about 14 wt % flavorant and about 57 wt % glycerol aerosol generating agent (DWB).

In another of these embodiments, the amorphous solid comprises about 29 wt % alginate gelling agent, about 9 wt % flavorant and about 60 wt % glycerol (DWB).

The amorphous solid of these embodiments may be included in a consumable or system as a shredded sheet, optionally blended with cut tobacco. Alternatively, the amorphous solid of these embodiments may be included in a consumable or system as a sheet, such as a sheet circumscribing a rod of aerosolizable material (e.g. tobacco). Alternatively, the amorphous solid of these embodiments may be included in a consumable or system as a layer portion disposed on a carrier.

In some embodiments, the amorphous solid comprises tobacco extract. In these embodiments, the amorphous solid may have the following composition (DWB): gelling agent (preferably comprising alginate) in an amount of from about 5 wt % to about 40 wt %, or about 10 wt % to 30 wt %, or about 15 wt % to about 25 wt %; tobacco extract in an amount of from about 30 wt % to about 60 wt %, or from about 40 wt % to 55 wt %, or from about 45 wt % to about 50 wt %; aerosol generating agent (preferably comprising glycerol) in an amount of from about 10 wt % to about 50 wt %, or from about 20 wt % to about 40 wt %, or from about 25 wt % to about 35 wt % (DWB).

In one embodiment, the amorphous solid comprises about 20 wt % alginate gelling agent, about 48 wt % Virginia tobacco extract and about 32 wt % glycerol (DWB).

The amorphous solid of these embodiments may have any suitable water content. For example, the amorphous solid may have a water content of from about 5 wt % to about 15 wt %, or from about 7 wt % to about 13 wt %, or about 10 wt %.

The amorphous solid of these embodiments may be included in a consumable or system as a shredded sheet, optionally blended with cut tobacco. Alternatively, the amorphous solid of these embodiments may be included in a consumable or system as a sheet, such as a sheet circumscribing a rod of aerosolizable material (e.g. tobacco).

Alternatively, the amorphous solid of these embodiments may be included in a consumable or system as a layer portion disposed on a carrier. Suitably, in any of these embodiments, the amorphous solid has a thickness of from about 50 μm to about 200 μm, or about 50 μm to about 100 μm, or about 60 μm to about 90 μm, suitably about 77 μm.

The slurry for forming this amorphous solid may also form part of the invention. In some cases, the slurry may have an elastic modulus of from about 5 to 1200 Pa (also referred to as storage modulus); in some cases, the slurry may have a viscous modulus of about 5 to 600 Pa (also referred to as loss modulus).

All percentages by weight described herein (denoted wt %) are calculated on a dry weight basis, unless explicitly stated otherwise. All weight ratios are also calculated on a dry weight basis. A weight quoted on a dry weight basis refers to the whole of the extract or slurry or material, other than the water, and may include components which by themselves are liquid at room temperature and pressure, such as glycerol. Conversely, a weight percentage quoted on a wet weight basis refers to all components, including water.

As used herein, the term "sheet" denotes an element having a width and length substantially greater than a thickness thereof. The sheet may be a strip, for example.

As used herein, the term "heating material" or "heater material" refers to material that is heatable by penetration with a varying magnetic field.

Induction heating is a process in which an electrically-conductive object is heated by penetrating the object with a varying magnetic field. The process is described by Faraday's law of induction and Ohm's law. An induction heater may comprise an electromagnet and a device for passing a varying electrical current, such as an alternating current, through the electromagnet. When the electromagnet and the object to be heated are suitably relatively positioned so that the resultant varying magnetic field produced by the electromagnet penetrates the object, one or more eddy currents are generated inside the object. The object has a resistance to the flow of electrical currents. Therefore, when such eddy currents are generated in the object, their flow against the electrical resistance of the object causes the object to be heated. This process is called Joule, ohmic, or resistive heating. An object that is capable of being inductively heated is known as a susceptor.

It has been found that, when the susceptor is in the form of a closed electrical circuit, magnetic coupling between the susceptor and the electromagnet in use is enhanced, which results in greater or improved Joule heating.

Magnetic hysteresis heating is a process in which an object made of a magnetic material is heated by penetrating the object with a varying magnetic field. A magnetic material can be considered to comprise many atomic-scale magnets, or magnetic dipoles. When a magnetic field penetrates such material, the magnetic dipoles align with the magnetic field. Therefore, when a varying magnetic field, such as an alternating magnetic field, for example as produced by an electromagnet, penetrates the magnetic material, the orientation of the magnetic dipoles changes with the varying applied magnetic field. Such magnetic dipole reorientation causes heat to be generated in the magnetic material.

When an object is both electrically-conductive and magnetic, penetrating the object with a varying magnetic field can cause both Joule heating and magnetic hysteresis heating in the object. Moreover, the use of magnetic material can strengthen the magnetic field, which can intensify the Joule and magnetic hysteresis heating.

In each of the above processes, as heat is generated inside the object itself, rather than by an external heat source by heat conduction, a rapid temperature rise in the object and more uniform heat distribution can be achieved, particularly through selection of suitable object material and geometry, and suitable varying magnetic field magnitude and orientation relative to the object. Moreover, as induction heating and magnetic hysteresis heating do not require a physical connection to be provided between the source of the varying magnetic field and the object, design freedom and control over the heating profile may be greater, and cost may be lower.

Referring to FIGS. 1 and 2, there are shown schematic cross-sectional side and end views of an example of a consumable according to an embodiment of the disclosure. The consumable 1 is for use with apparatus for heating aerosolizable material to volatilize at least one component of the aerosolizable material, such as the apparatus 100 shown in FIG. 8 and described below.

The consumable 1 comprises a hollow tube comprising a carrier 16 and aerosolizable material 14 comprising an amorphous solid that has been coated on the carrier 16. The aerosolizable material 14 may be considered a coating on the carrier 16. The aerosolizable material 14 may have been sprayed, electro-sprayed, cast or band casted onto the carrier 16, for example. The hollow tube is located around an air gap 10 of the consumable 1. In this embodiment, the air gap 10 is formed by a through hole that extends from one longitudinal end to an opposite longitudinal end of the consumable 1. In other embodiments, the air gap 10 may be formed by a blind hole that extends only partially from one longitudinal end of the consumable 1 towards the opposite longitudinal end of the consumable 1.

The hollow tube of the consumable 1 extends along an axis A-A. The axis A-A is a central axis that extends along the air gap 10, but in other embodiments the configuration of the hollow tube may be such that the axis A-A is offset from the air gap 10. In this embodiment, the hollow tube is elongate in the direction of the axis A-A, but in other embodiments a width or diameter of the hollow tube may be greater than or equal to a dimension of the hollow tube in the direction of the axis A-A, so that the hollow tube is not elongate. The hollow tube of this embodiment has circular inner and outer cross-sectional shapes. In other embodiments, one or other of the inner and outer cross-sectional shapes of the hollow tube may be other than circular, such as elliptical, polygonal, rectangular, square, triangular, or star-shaped.

In some embodiments, the carrier 16 forms at least part of a surface, such as an outermost surface, of the hollow tube or of the whole consumable. In some embodiments, the carrier 16 forms at least a majority of the surface, such as all of the surface. In this embodiment, the carrier 16 forms an outermost surface of the hollow tube and of the consumable 1. This can help to keep a user's fingers or hands free from having to contact the aerosolizable material 14 during manipulation of the consumable, such as when inserting or removing the consumable from an apparatus with which it is usable. It can also help avoid the aerosolizable material 14 contacting a wall defining a heating zone of the apparatus, which can help keep the apparatus relatively clean. However, in other embodiments, such as that described below with reference to FIG. 3, the carrier 16 additionally or alternatively forms an innermost surface of the hollow tube and/or of the consumable.

The carrier 16 in this embodiment is tubular. Moreover, in this embodiment the carrier 16 encircles the aerosolizable material 14 and the air gap 10, with the aerosolizable material 14 located between the carrier 16 and the air gap 10. In some other embodiments, the carrier 16 may be other than tubular. For example, in some embodiments, the carrier 16 may have an axially-extending slot or other feature formed therein, so that the carrier 16 has a circumferential discontinuity and thus does not form a complete tube.

The carrier 16 may be made of any suitable material. The carrier 16 should be sufficiently heat resistant to withstand temperatures to which it is subjected in normal use of the consumable 1, such as the temperatures discussed later herein. The carrier 16 may help to provide the consumable 1 with rigidity. In some embodiments, the carrier 16 is non-porous to aerosol generated from the aerosolizable material 14 in use. In some embodiments, the carrier 16 comprises one or more materials selected from the group consisting of: paper, card, paperboard, cardboard, reconstituted tobacco, a plastics material, a metal, and a metal alloy. For example, in some embodiments, the carrier 16 may comprise a wound sheet or strip, for example of paper or card or reconstituted tobacco. In some embodiments, the carrier 16 comprises a laminate of any two of the materials listed above, such as paper and metal or metal alloy. In other embodiments, the carrier 16 may comprise an extrudate, for example of a plastics material or a material comprising one or more metals or metal alloys. In some embodiments, the carrier 16 comprises or consists of a tobacco material, such as a sheet of reconstituted tobacco.

In one case, a surface of the carrier 16 that abuts the aerosolizable material 14 may be porous. For example, in some cases, the carrier 16 comprises paper. The inventors have found that a porous carrier such as paper is particularly suitable for the present invention; the porous layer abuts the aerosolizable material 14 and forms a strong bond. The amorphous solid of the aerosolizable material 14 is formed by drying a gel and, without being limited by theory, it is thought that the slurry from which the gel is formed partially impregnates the porous carrier (e.g. paper) so that when the gel sets and forms cross-links, the carrier is partially bound into the gel. This provides a strong binding between the gel and the carrier (and between the dried gel and the carrier). The porous layer (e.g. paper) may also be used to carry flavors. In some cases, the porous layer may comprise paper, suitably having a porosity of 0-300 Coresta Units (CU), suitably 5-100 CU or 25-75 CU.

Additionally, surface roughness may contribute to the strength of bond between the aerosolizable material 14 and the carrier 16. The inventors have found that the paper roughness (for the surface abutting the aerosolizable material) may suitably be in the range of 50-1000 Bekk seconds, suitably 50-150 Bekk seconds, suitably 100 Bekk seconds (measured over an air pressure interval of 50.66-48.00 kPa). (A Bekk smoothness tester is an instrument used to determine the smoothness of a paper surface, in which air at a specified pressure is leaked between a smooth glass surface and a paper sample, and the time (in seconds) for a fixed volume of air to seep between these surfaces is the "Bekk smoothness".)

In some embodiments, at least part of the aerosolizable material 14 is located radially inwards of the carrier 16. In some embodiments, such as that of FIGS. 1 and 2, all of the aerosolizable material 14 is located radially inwards of the carrier 16. In other embodiments, part of the aerosolizable material 14 may be located other than radially inwards of the carrier 16, such as on a longitudinal end face of the carrier 16 or on two opposite longitudinal end faces of the carrier 16. In some embodiments, such as that described below with reference to FIG. 3, at least part of the aerosolizable material 14 is located radially outwards of the carrier 16.

In some embodiments, the aerosolizable material 14 forms at least part of a surface, such as an innermost surface, of the hollow tube. The aerosolizable material 14 may form at least a majority of the surface of the hollow tube, such as all of the surface of the hollow tube. In this embodiment, the aerosolizable material 14 forms an innermost surface of the hollow tube. This may help enable aerosol to be delivered to a user via the air gap 10 in use. This, in turn, may help to reduce or avoid deposition of condensate in the apparatus in use. However, in other embodiments, such as that described below with reference to FIG. 3, the aerosolizable material 14 additionally or alternatively forms an outermost surface of the hollow tube. In some embodiments, the aerosolizable material 14 may form no part of an innermost surface of the hollow tube. For example, in some variations to the embodiment shown in FIGS. 1 and 2, the hollow tube may comprise another layer (not shown) that forms the innermost surface of the hollow tube, and that may be porous to aerosol generated from the aerosolizable material 14 in use.

As noted above, the aerosolizable material 14 in this embodiment is affixed to the carrier 16 by way of having been coated onto the carrier 16. The coating may have comprised spraying. The coating may have comprised casting. The casting may have involved providing material in liquid or other fluid form on a surface of the carrier 16 (or material that ultimately will form the carrier 16), and then allowing the material to at least partially solidify or cure on the surface of the carrier 16 to form the aerosolizable material 14 comprising an amorphous solid. The aerosolizable material 14 in such an embodiment may itself be called a "casting".

In other embodiments, the aerosolizable material 14 comprising an amorphous solid may be affixed to the carrier 16 by a mechanism other than coating. For example, in some embodiments, the aerosolizable material 14 may be affixed to the carrier 16 through the provision of an adhesive between the aerosolizable material 14 and the carrier 16. The adhesive may comprise one or more of, for example, gum Arabic, natural or synthetic resins, starches, polyvinyl acetate (PVA), and varnish. In other embodiments, the affixation may be by way of providing a fastener or an interference fit between the aerosolizable material 14 and the carrier 16 such that the aerosolizable material 14 is retained in position relative to the carrier 16. In some embodiments, the aerosolizable material 14 may be affixed to the carrier 16 by way of being trapped or sandwiched between two layers of the carrier 16, or between two carriers 16.

In this embodiment, the aerosolizable material 14 is tubular. More specifically, in this embodiment the aerosolizable material 14 is affixed along an annular path on an inside surface of the carrier 16 so that the aerosolizable material 14 encircles the air gap 10. In this embodiment, the aerosolizable material 14 covers all, or substantially all, of the inside surface of the carrier 16. In other embodiments, the inside surface of the carrier 16 may be only partly covered by the aerosolizable material 14. For example, the aerosolizable material 14 may be coated or otherwise affixed on the carrier 16 as one or more discrete and spaced-apart regions, such as tubes, of aerosolizable material 14. In some embodiments, the aerosolizable material 14 may be non-tubular, such as in the form of one or more patches on the carrier 16.

The consumable 1 of this embodiment is suitable for insertion into a heating zone of an apparatus, such as the heating zone 110 of the apparatus 100 shown in FIG. 8, wherein the apparatus has a device for causing heating of the aerosolizable material 14 when the consumable 1 is in the heating zone. Once in the heating zone 110, the device of the apparatus causes heating of the aerosolizable material 14 to volatilize at least one component of the aerosolizable material 14. In some embodiments, the device may be configured to apply heat energy to the consumable 1, and specifically to the aerosolizable material 14 via the carrier 16. In some such embodiments, the device comprises a resistive heater that is heated by electrically connecting the resistive heater to a supply of electricity, and heat energy passes from the resistive heater to the consumable 1. In some other embodiments, the device may comprise a magnetic field generator 112 for generating a varying magnetic field for penetrating the heating zone when the consumable 1 is in the heating zone 110, and the carrier 16 of the consumable 1 comprises heating material that is heatable by penetration with the varying magnetic field. Accordingly, in those other embodiments, the device is configured to cause electromagnetic energy to be applied to the heating material of the consumable 1 to create heat in the heating material, and then heat energy is applied from the carrier 16 to the aerosolizable material 14. In some embodiments, the consumable 1 may comprise heating material that is partially or fully embedded in the aerosolizable material 14. In still further embodiments, the apparatus 100 has a heatable element 120 comprising heating material, wherein the heatable element 120 is in thermal contact with the heating zone 110, and wherein the magnetic field generator 112 is for generating a varying magnetic field for penetrating the heatable element 120 so as to cause heating of the heatable element 120 and thus the heating zone 110. In any event, the volatilized component(s) of the aerosolizable material 14 then pass from the aerosolizable material 14 and into the air gap 10, where they may form an aerosol, and from there may pass out of the consumable 1 by a user drawing on the consumable 1 or a mouthpiece (when provided) of the apparatus 100.

It will therefore be understood that, in some embodiments, the carrier 16 comprises heating material that is heatable by penetration with a varying magnetic field. The heating material may for example be any one or more of those discussed herein. The carrier 16 may consist of, or substantially consist, of the heating material. It is preferable, though not essential, for the carrier 16 to comprise a closed circuit of the heating material. The heating material may have a substantially constant cross-sectional area with axial distance along the consumable 1. However, in other embodiments, the carrier 16 may be free from such heating material. Indeed, in some embodiments, the whole consumable may be free from such heating material.

Referring to FIG. 3, there is shown a schematic cross-sectional end view of an example of a consumable according to another embodiment of the disclosure. The consumable 2 is for use with apparatus for heating aerosolizable material to volatilize at least one component of the aerosolizable material, such as the apparatus 100 shown in FIG. 8 and described below. The consumable 2 comprises a hollow tube comprising a carrier 16 and aerosolizable material 14 comprising an amorphous solid coated on the carrier 16. The hollow tube is located around an air gap 10 of the consumable 2.

It will be noted that the consumable 2 of FIG. 3 is similar to the consumable 1 of FIGS. 1 and 2, and like elements are indicated with like reference numerals. In the interests of brevity, discussion of the consumable 2 of FIG. 3 will focus primarily on the differences between the two consumables 1, 2. However, it is to be noted that any of the possible variations to the consumable 1 (or parts thereof) of FIGS. 1 and 2 discussed herein may be made to the consumable 2 (or corresponding parts thereof) of FIG. 3 to form further embodiments.

In this embodiment, although not expressly shown in FIG. 3, the hollow tube of the consumable 2 again is elongate in the direction of a central axis A-A that extends along the air gap 10, and the hollow tube has circular inner and outer cross-sectional shapes. However, in this embodiment, the aerosolizable material 14 is located radially outwards of the carrier 16. In some embodiments, such as that of FIG. 3, all of the aerosolizable material 14 is located radially outwards of the carrier 16. In other embodiments, part of the aerosolizable material 14 may be located other than radially outwards of the carrier 16, such as on a longitudinal end face of the carrier 16 or on two opposite longitudinal end faces of the carrier 16.

The aerosolizable material 14 is affixed to the carrier 16 by way of having been coated onto the carrier 16. The coating may have comprised spraying or casting. In this embodiment the carrier 16 forms an innermost surface of the hollow tube and of the consumable 2, and the aerosolizable material 14 forms an outermost surface of the hollow tube and of the consumable 2. The aerosolizable material 14 in this embodiment is tubular. Moreover, in this embodiment the aerosolizable material 14 encircles the carrier 16 and the air gap 10, with the carrier 16 located between the aerosolizable material 14 and the air gap 10. In this embodiment, the aerosolizable material 14 covers all, or substantially all, of an outside surface of the carrier 16. In other embodiments, the outside surface of the carrier 16 may be only partly covered by the aerosolizable material 14. For example, the aerosolizable material 14 may be coated on the carrier 16 as one or more discrete and spaced-apart regions, such as tubes, of aerosolizable material 14. In some embodiments, the aerosolizable material 14 may be non-tubular, such as in the form of one or more patches on the carrier 16.

The consumable 2 of this embodiment is suitable for insertion into a heating zone of an apparatus that has a device for causing heating of the aerosolizable material 14 when the consumable 2 is in the heating zone. Once in the heating zone, the device of the apparatus causes heating of the aerosolizable material 14 using any of the heating techniques discussed herein to volatilize at least one component of the aerosolizable material 14. In some embodiments, the device of the apparatus may project into the air gap 10 of the consumable 2 when the consumable 2 is in the heating zone, and the device may be configured to apply heat energy to the aerosolizable material 14 via the carrier 16. Once volatilized, the component(s) of the aerosolizable material 14 then pass radially outwards from the aerosolizable material 14 and the consumable 2, where they may form an aerosol, and a user may draw on the consumable 2 or a mouthpiece of the apparatus to inhale the volatilized component(s) or aerosol.

Referring to FIG. 4, there is shown a schematic cross-sectional end view of an example of a consumable according to another embodiment of the disclosure. The consumable 3 is for use with apparatus for heating aerosolizable material to volatilize at least one component of the aerosolizable material, such as the apparatus 100 shown in FIG. 8 and described below. The consumable 3 comprises a hollow tube comprising a carrier 16 and aerosolizable material 14 comprising an amorphous solid coated on the carrier 16. The hollow tube is located around an air gap 10 of the consumable 3.

The consumable 3 of FIG. 4 is identical to the consumable 1 of FIGS. 1 and 2 except for the form of the carrier 16.

Accordingly, like elements are indicated with like reference numerals and, in the interests of brevity, discussion of the consumable 3 of FIG. 4 will focus primarily on the differences between the two consumables 1, 3. It is to be noted that any of the possible variations to the consumable 1 (or parts thereof) of FIGS. 1 and 2 discussed herein may be made to the consumable 3 (or corresponding parts thereof) of FIG. 4 to form further embodiments.

The consumable 3, and more particularly the carrier 16, of this embodiment comprises heating material that is heatable by penetration with a varying magnetic field to thereby heat the aerosolizable material 14. The heating material may for example be any one or more of those discussed herein.

More specifically, the carrier 16 comprises a first layer 18 comprising the heating material, and a second layer 20. The carrier 16 may be a laminate. It is preferable, though not essential, for the carrier 16 (e.g. the first layer 18 thereof) to comprise heating material, such as a closed circuit of heating material. The heating material may for example be any one or more of those discussed herein. In this embodiment, the second layer 20 is not heatable by penetration with a varying magnetic field, but in other embodiments the second layer 20 may also comprise heating material that may be the same as or different to the heating material of the first layer 18. The second layer may, for example, comprise one or more materials selected from the group consisting of: paper, card, paperboard, cardboard, reconstituted tobacco, and a plastics material.

In this embodiment, the first layer 18 is located between the aerosolizable material 14 and the second layer 20. The aerosolizable material 14 is coated on the first layer 18, and the second layer 20 forms an outermost surface of the tubular member and the consumable 3.

In other embodiments, the second layer 20 may be located between the aerosolizable material 14 and the first layer 18 comprising the heating material. In some such other embodiments, the aerosolizable material 14 may be coated on the second layer 20, and the first layer 18 may form the outermost surface of the tubular member and the consumable 3. In still further embodiments, the carrier 16 may comprise one or more further layers (not shown), at least one of which forms the outermost surface of the tubular member, and optionally of the consumable 3. In some such embodiments, the first layer 18 comprising the heating material may be located between the second layer 20 and the one or more further layers. Moreover, in some such embodiments, the aerosolizable material 14 may be coated on the second layer 20 and/or on the one or more further layers. Still further arrangements may be apparent to the skilled person. In variations to each of these described embodiments, the aerosolizable material 14 may be affixed to the carrier 16 by a mechanism other than coating, such as any of the techniques discussed herein in relation to the consumable 1 of FIGS. 1 and 2.

The consumable 3 of this embodiment is suitable for insertion into a heating zone of an apparatus that has a device for causing heating of the aerosolizable material 14 when the consumable 3 is in the heating zone. Once in the heating zone, the device of the apparatus causes heating of the aerosolizable material 14 using any of the heating techniques discussed herein to volatilize at least one component of the aerosolizable material 14. The volatilized component(s) of the aerosolizable material 14 then pass from the aerosolizable material 14 and into the air gap 10, where they may form an aerosol, and from there may pass out of the consumable 3 by a user drawing on the consumable 3 or a mouthpiece (when provided) of the apparatus.

As noted above, the consumable 3 of FIG. 4 is identical to the consumable 1 of FIGS. 1 and 2 except for the form of the carrier 16. In a similar way, in some embodiments, the consumable may be identical to the consumable 2 of FIG. 3 except for the form of the carrier 16. For example, in some embodiments, the consumable 2 of FIG. 3 may be modified so that the carrier 16 comprises a first layer comprising heating material, and a second layer. The heating material may for example be any one or more of those discussed herein. In some embodiments, the second layer may not be heatable by penetration with a varying magnetic field. In other embodiments, the second layer may comprise heating material that may be the same as or different to the heating material of the first layer. The second layer may, for example, comprise one or more materials selected from the group consisting of: paper, card, paperboard, cardboard, reconstituted tobacco, and a plastics material. In some embodiments, the first layer is located between the aerosolizable material 14 and the second layer. In some embodiments, the aerosolizable material 14 is coated on the first layer, and the second layer forms the innermost surface of the tubular member and the consumable. In other embodiments, the second layer may be located between the aerosolizable material 14 and the first layer comprising the heating material. In some such other embodiments, the aerosolizable material 14 may be coated on the second layer, and the first layer may form the innermost surface of the tubular member and the consumable. In still further embodiments, the carrier 16 may comprise one or more further layers (not shown), at least one of which forms the innermost surface of the tubular member, and optionally of the consumable. In some such embodiments, the first layer comprising the heating material may be located between the second layer and the one or more further layers. Moreover, in some such embodiments, the aerosolizable material 14 may be coated on the second layer and/or on the one or more further layers. Still further arrangements may be apparent to the skilled person.

Referring to FIG. 5, there is shown a schematic cross-sectional end view of an example of a consumable according to another embodiment of the disclosure. The consumable 4 is for use with apparatus for heating aerosolizable material to volatilize at least one component of the aerosolizable material, such as the apparatus 100 shown in FIG. 8 and described below. The consumable 4 comprises a hollow tube comprising a carrier 16 and aerosolizable material 14 comprising an amorphous solid coated on the carrier 16. The hollow tube is located around an air gap 10 of the consumable 4.

It will be noted that the consumable 4 of FIG. 5 is similar to the consumable 2 of FIG. 3, and like elements are indicated with like reference numerals. In the interests of brevity, discussion of the consumable 4 of FIG. 5 will focus primarily on the differences between the two consumables 2, 4. However, it is to be noted that any of the possible variations to the consumable 2 (or parts thereof) of FIG. 3 discussed herein may be made to the consumable 4 (or corresponding parts thereof) of FIG. 5 to form further embodiments. For example, the carrier 16 may be of the form of any of the carriers 16 discussed herein, such that in some embodiments the carrier 16 comprises heating material that is heatable by penetration with a varying magnetic field to heat the aerosolizable material 14. The heating material may for example be any one or more of those discussed herein. In other embodiments, the carrier 16 may be free from such heating material. Indeed, in some embodiments, the whole consumable 4 may be free from such heating material.

The consumable 4 comprises a body of porous aerosol containment material 11. In this embodiment, the hollow tube comprises the body of porous aerosol containment material 11. More specifically, in this embodiment, the aerosolizable material 14 is located radially between the carrier 16 and the body of porous aerosol containment material 11. Still more specifically, in this embodiment the body of porous aerosol containment material 11 is located radially outwards of the aerosolizable material 14. In some embodiments, at least part of the body of porous aerosol containment material 11 may be located on a longitudinal end face of the aerosolizable material 14 or on two opposite longitudinal end faces of the aerosolizable material 14.

The body of porous aerosol containment material 11 is for containing aerosol generated from the aerosolizable material 14 during heating of the aerosolizable material 14 in use. The porous aerosol containment material 11 may help to ensure that volatilized material generated from the aerosolizable material 14 in use does not condense on a surface of the apparatus 100 with which the consumable 4 used. In some embodiments, the provision of the body of porous aerosol containment material 11 helps to increase the surface area on which aerosol generated from the aerosolizable material 14 in use may form in the consumable 4. In some embodiments, such a body of porous aerosol containment material 11 helps to increase the amount of visible aerosol generated from the aerosolizable material 14 in use, and thus may enhance the consumer experience.

In some embodiments, the body of porous aerosol containment material 11 is free from aerosolizable material. In some embodiments, the porous aerosol containment material 11 comprises one or more materials selected from the group consisting of: wadding, fleece, non-woven material, non-woven fleece, woven material, knitted material, nylon, foam, polystyrene, polyester, polyester filament, polypropylene, and a blend of polyester and polypropylene. In other embodiments, the body of porous aerosol containment material 11 may comprise aerosolizable material.

In this embodiment, the aerosolizable material 14 is in contact with the body of porous aerosol containment material 11, but in other embodiments there may be a further layer of material between the aerosolizable material 14 and the body of porous aerosol containment material 11. Such a further layer of material may increase the rigidity or robustness of the consumable 4, may help retain the relative positions of the aerosolizable material 14 and the porous aerosol containment material 11, and/or may help hold different regions of the aerosolizable material 14 together. Such a further layer of material should be porous to the aerosol generated from the aerosolizable material 14, so that the aerosol is able to reach the porous aerosol containment material 11.

In this embodiment, the body of porous aerosol containment material 11 is tubular. Moreover, in this embodiment the body of porous aerosol containment material 11 encircles the aerosolizable material 14, the carrier 16 and the air gap 10, with the aerosolizable material 14 located between the carrier 16 and the body of porous aerosol containment material 11. In some other embodiments, the body of porous aerosol containment material 11 may be other than tubular. For example, in some embodiments, the body of porous aerosol containment material 11 may have an axially-extending slot or other feature formed therein, so that the body of porous aerosol containment material 11 has a circumferential discontinuity and thus does not form a complete tube.

The consumable 4 of FIG. 5 also comprises an outer cover 12. In this embodiment, the outer cover 12 is tubular. Moreover, in this embodiment the outer cover 12 encircles the body of porous aerosol containment material 11, with the body of porous aerosol containment material 11 located between the outer cover 12 and the aerosolizable material 14.

The outer cover 12 may be made of any suitable material. The outer cover 12 should be sufficiently heat resistant to withstand temperatures to which it is subjected in normal use, such as the temperatures discussed later herein. In some embodiments, the outer cover 12 is non-porous to aerosol generated from the aerosolizable material 14 in use. For example, in some embodiments, volatilized material generated from the aerosolizable material 14 and contained in the body of porous aerosol containment material 11 in use is directed by the outer cover 12 to pass out of the consumable 4 via an axial end of the body of porous aerosol containment material 11.

In some embodiments, the outer cover 12 comprises one or more materials selected from the group consisting of: paper, card, paperboard, cardboard, reconstituted tobacco, a plastics material, a metal, and a metal alloy. For example, in some embodiments, the outer cover 12 may comprise a wound sheet or strip, for example of paper or card or reconstituted tobacco. In other embodiments, the outer cover 12 may comprise an extrudate, for example of a plastics material or a material comprising one or more metals.

In some other embodiments, the outer cover 12 may be other than tubular, or omitted from the consumable 4.

In variations to the embodiments of FIGS. 1 to 4, the consumable 1, 2, 3 may comprise a body of porous aerosol containment material 11 for containing aerosol generated from the aerosolizable material 14 during heating of the aerosolizable material 14 in use. In some such variations, the aerosolizable material 14 may be located radially between the carrier 16 and the body of porous aerosol containment material 11. In some such embodiments, the consumable 1, 2, 3 also comprises a cover 12, with the body of porous aerosol containment material 11 located between the cover 12 and the aerosolizable material 14.

Referring to FIG. 6, there is shown a schematic cross-sectional end view of an example of a consumable according to another embodiment of the disclosure. The consumable 5 is for use with apparatus for heating aerosolizable material to volatilize at least one component of the aerosolizable material, such as the apparatus 100 shown in FIG. 8 and described below. The consumable 5 comprises a hollow tube comprising a carrier 16 and aerosolizable material 14 comprising an amorphous solid coated on the carrier 16. The hollow tube is located around an air gap 10 of the consumable 5.

It will be noted that the consumable 5 of FIG. 6 is similar to the consumable 2 of FIG. 3, and like elements are indicated with like reference numerals. In the interests of brevity, discussion of the consumable 5 of FIG. 6 will focus primarily on the differences between the two consumables 2, 5. However, it is to be noted that any of the possible variations to the consumable 2 (or parts thereof) of FIG. 3 discussed herein may be made to the consumable 5 (or corresponding parts thereof) of FIG. 6 to form further embodiments. For example, the carrier 16 may be of the form of any of the carriers 16 discussed herein, such that in some embodiments the carrier 16 comprises heating material that is heatable by penetration with a varying magnetic field to heat the aerosolizable material 14. The heating material may for example be any one or more of those discussed herein. In other embodiments, the carrier 16 may be free from such heating material. Indeed, in some embodiments, the whole consumable 5 may be free from such heating material.

The carrier 16 of this embodiment forms an innermost surface of the consumable 5. In other embodiments, the carrier 16 may form only a part of the innermost surface. The carrier 16 of this embodiment also has a plurality of holes 16a extending therethrough for permitting aerosol generated from the aerosolizable material 14 during heating of the aerosolizable material 14 in use to pass to the innermost surface of the consumable 5. In other embodiments, there may be only one such hole 16a. The, or each, hole 16a may take any suitable form, such as a perforation in the carrier 16.

The consumable 5 of this embodiment has an outer cover 12. In this embodiment, the outer cover 12 encircles the aerosolizable material 14, with the aerosolizable material 14 located between the outer cover 12 and the carrier 16. The outer cover 12 may take any of the forms discussed herein for the outer cover 12 of the consumable 4 of FIG. 5. However, in some embodiments, the outer cover 12 is non-porous to aerosol generated from the aerosolizable material 14 in use. For example, in some embodiments, volatilized material generated from the aerosolizable material 14 is directed by the outer cover 12 to pass out of the consumable 4 generally radially inwards to the air gap 10 via one or more of the hole(s) 16a that extend through the carrier 16. From the air gap 10, the aerosol may pass out of the consumable 5 by a user drawing on the consumable 5 or a mouthpiece (when provided) of the apparatus 100.

In other embodiments, the locations of the carrier 16 and the cover 12 may be reversed, so that the cover 12 directs volatilized material generated from the aerosolizable material 14 to pass out of the consumable 4 in a generally radially outwards direction via the one or more of the hole(s) 16a that extend through the carrier 16.

In some embodiments, the consumable 1, 2, 3, 4, 5 also comprises a filter (not shown). The filter may be for filtering aerosol or vapor released from the aerosolizable material 14 in use. Alternatively, or additionally, the filter may be for controlling the pressure drop over a length of the consumable 1, 2, 3, 4, 5. The filter could be of any type used in the tobacco industry. For example, the filter may be made of cellulose acetate. In some embodiments, the filter is substantially cylindrical with a substantially circular cross section and a longitudinal axis. In other embodiments, the filter may have a different cross section or not be elongate.

In some embodiments, the filter abuts a longitudinal end of the hollow tube and is axially aligned with the hollow tube. In other embodiments, the filter may be spaced from the hollow tube, such as by a gap and/or by one or more further components of the consumable 1, 2, 3, 4, and 5. Example further component(s) are an additive or flavor source (such as an additive- or flavor-containing capsule or thread), which may be held by a body of filtration material or between two bodies of filtration material, for example.

The consumable 1, 2, 3, 4, 5 may also comprise a wrap that is wrapped around the hollow tube and the filter to retain the filter relative to the hollow tube. The wrap may encircle the hollow tube and the filter. The wrap may be wrapped around the hollow tube and the filter so that free ends of the wrap overlap each other. The wrap may form part of, or all of, a circumferential outer surface of the consumable 1, 2, 3, 4, and 5. The wrap could be made of any suitable material, such as paper, card, or reconstituted aerosolizable material (e.g. reconstituted tobacco). The wrap may also comprise an adhesive (not shown), such as one of those discussed elsewhere herein, that adheres the overlapped free ends of the wrap to each other. The adhesive helps prevent the overlapped free ends of the wrap from separating. In other embodiments, the adhesive may be omitted or the wrap may take a different from to that described. In other embodiments, the filter may be retained relative to the hollow tube by a connector other than a wrap, such as an adhesive.

In some embodiments, the consumable 1, 2, 3, 4, 5 may have a length in the axial direction of between 30 millimeters and 150 millimeters, such as between 70 millimeters and 120 millimeters.

In some embodiments, the hollow tube may have an inner dimension (e.g. an inner diameter) in a direction perpendicular to the axial direction of between 2 millimeters and 10 millimeters, such as between 4 millimeters and 8 millimeters.

In some embodiments, the hollow tube may have an outer dimension (e.g. an outer diameter) in a direction perpendicular to the axial direction of between 4 millimeters and 10 millimeters, such as between 4.5 millimeters and 8 millimeters.

In some embodiments, the hollow tube may have a thickness in a direction perpendicular to the axial direction of between 0.15 millimeters and 0.5 millimeters, such as between 0.2 millimeters and 0.3 millimeters.

In some embodiments, the aerosolizable material 14 may have a thickness in a direction perpendicular to the axial direction of the consumable of less than or equal to 1 millimeter, such as less than or equal to 0.5 millimeters, or less than or equal to 0.25 millimeters, or less than or equal to 0.2 millimeters, or less than or equal to 0.1 millimeters, or less than or equal to 0.05 millimeters. The thickness may be between 0.05 millimeters and 1.0 millimeter. In some embodiments, the aerosolizable material 14 comprising an amorphous solid is provided as a thin film coated on, or otherwise affixed to, the carrier 16.

Referring to FIG. 7, there is shown a flow diagram showing an example of a method of manufacturing a consumable for use with apparatus for heating aerosolizable material to volatilize at least one component of the aerosolizable material, according to an embodiment of the disclosure. The method of FIG. 7 is usable to manufacture any of the consumables described herein.

The method comprises providing 72 a hollow tube comprising a carrier and aerosolizable material comprising an amorphous solid affixed to the carrier. The carrier may be any one of the carriers 16 discussed herein, for example. Similarly, the aerosolizable material may be any one of the aerosolizable materials 14 discussed herein, for example.

In some embodiments, the providing 72 comprises affixing 74 the aerosolizable material 14 to the carrier 16, and then forming 76 the hollow tube. Accordingly, in some embodiments, the carrier 16 may be flat or substantially flat at the time the aerosolizable material 14 is affixed to it. Thereafter, in some embodiments, the carrier 16 and aerosolizable material 14 may be manipulated together during formation of the hollow tube. Such manipulation may comprise rolling or wrapping the combination of the carrier 16 and aerosolizable material 14 into a tubular, or substantially tubular, form. Such rolling or wrapping may be around a mandrel, for example. In other embodiments, the carrier 16 is provided in a tubular, or substantially tubular, form, and thereafter the aerosolizable material 14 is affixed to the carrier 16.

In some embodiments, the method comprises manufacturing the carrier 16. For example, and as discussed by way of some examples herein, the carrier 16 may comprise a plurality of layers, and the manufacture of the carrier 16 may comprise assembling those layers to form the carrier 16, such as by adhesion. At least one of the layers may be in sheet or strip form. At least one of the layers may comprise heating material, such as one or more of any of the example heating materials discussed herein. At least one of the layers may not itself be heatable by penetration with a varying magnetic field.

In some embodiments, such as some of those in which the affixing 74 is performed before the forming 76, the affixing 74 comprises coating the aerosolizable material 14 onto the carrier 16. As discussed elsewhere herein, such coating may comprise spraying, electro-spraying, casting or band casting, for example. As discussed elsewhere herein, such casting may involve providing material in liquid or other fluid form on a surface of the carrier 16 (or material that ultimately will form the carrier 16), and then allowing the material to at least partially solidify or cure on the surface of the carrier 16 to form the aerosolizable material 14 comprising an amorphous solid. The material in liquid or other fluid form may be aerosolizable in that form, or may only become aerosolizable once it has solidified or cured.

In some embodiments, the affixing 74 may comprise a technique other than coating. For example, in some embodiments, the affixing 74 comprises adhering the aerosolizable material 14 to the carrier 16 using an adhesive, such as any of those discussed herein.

In some embodiments, the aerosolizable material 14 forms at least part of a surface of the hollow tube. In some embodiments, the aerosolizable material 14 forms all of the surface of the hollow tube. In some embodiments, the surface is an innermost surface of the hollow tube.

Referring to FIG. 8, there is shown a schematic view of an example of a system comprising a consumable and apparatus for heating aerosolizable material of the consumable to volatilize at least one component of the aerosolizable material, according to an embodiment of the disclosure.

The system 1000 comprises the consumable 1 of FIGS. 1 and 2 and apparatus 100 for heating the aerosolizable material 14 of the consumable 1 to volatilize at least one component of the aerosolizable material 14. In other embodiments, the consumable 1 may be replaced by any of the other consumables described herein, such as consumables 2, 3, 4, 5 shown in FIGS. 3 to 6. In this embodiment, the apparatus 100 is a tobacco heating product (also known in the art as a tobacco heating device or a heat-not-burn device).

The apparatus comprises a heating zone 110 for receiving the consumable 1, 2, 3, 4, 5, and a device 112 for causing heating of the aerosolizable material 14 when the consumable 1, 2, 3, 4, 5 is in the heating zone 110.

The apparatus 100 may define an air inlet (not shown) that fluidly connects the heating zone 110 with the exterior of the apparatus 100. A user may be able to inhale the volatilized component(s) of the aerosolizable material by drawing the volatilized component(s) from the heating zone 110. As the volatilized component(s) are removed from the heating zone 110 and the consumable 1, 2, 3, 4, 5, air may be drawn into the heating zone 110 via the air inlet of the apparatus 100.

In this embodiment, the heating zone 110 comprises a recess for receiving at least a portion of the consumable 1, 2, 3, 4, 5. In other embodiments, the heating zone 110 may be other than a recess, such as a shelf, a surface, or a projection, and may require mechanical mating with the consumable 1, 2, 3, 4, 5 in order to co-operate with, or receive, the consumable 1, 2, 3, 4, 5. In this embodiment, the heating zone 110 is elongate, and is sized and shaped to accommodate the whole consumable 1, 2, 3, 4, 5. In other embodiments, the heating zone 110 may be dimensioned to receive only a portion of the consumable 1, 2, 3, 4, 5.

In some embodiments, the device 112 comprises an electrical power source, a resistive heater that is heated by passing electricity through the resistive heater, and a controller for controlling the passage of electricity through the resistive heater. The resistive heater is configured to apply heat energy to the heating zone 110, and thus to the consumable 1, 2, 3, 4, 5 when the consumable is in the heating zone 110. The resistive heater may cause the heat energy to be applied to the aerosolizable material 14 via the carrier 16. In some embodiments, the resistive heater may project into the heating zone 110 so as to be located in the air gap 10 of the consumable when the consumable is in the heating zone 110. For example, such a configuration may be used when the consumable is one of those of FIG. 3 or FIG. 5. In some other embodiments, the resistive heater may be located radially outwards of the consumable when the consumable is in the heating zone 110. For example, the resistive heater may at least partially define the heating zone 110. Such a configuration may be used when the consumable is one of those of FIGS. 1, 2, 4 and 6, for example. In some embodiments, the device may comprise a first resistive heater that is in the air gap 10 of the consumable when the consumable is in the heating zone 110, and a second resistive heater that is located radially outwards of the consumable when the consumable is in the heating zone 110. For example, such a configuration may be used when the consumable is that of FIG. 5.

In some embodiments, such as that shown in FIG. 8, the device 112 comprises a magnetic field generator for generating a varying magnetic field for penetrating the heating zone 110 when the consumable is in the heating zone 110. Such apparatus 100 is suitable for use when the consumable comprises heating material for use in heating the aerosolizable material 14.

In this embodiment, the magnetic field generator 112 comprises an electrical power source 113, a coil 114, a device 116 for passing a varying electrical current, such as an alternating current, through the coil 114, a controller 117, and a user interface 118 for user-operation of the controller 117.

The electrical power source 113 of this embodiment is a rechargeable battery. In other embodiments, the electrical power source 113 may be other than a rechargeable battery, such as a non-rechargeable battery, a capacitor, a battery-capacitor hybrid, or a connection to a mains electricity supply.

The coil 114 may take any suitable form. In some embodiments, the coil 114 is a helical coil of electrically-conductive material, such as copper. In some embodiments, the coil is a flat coil. That is, the coil may be a two-dimensional spiral of electrically-conductive material, such as copper. In some embodiments, the coil 114 encircles the heating zone 110. In some embodiments, the coil 114 extends along a longitudinal axis that is substantially aligned with a longitudinal axis of the heating zone 110. The aligned axes may be coincident. Alternatively, the aligned axes may be parallel or oblique to each other.

In this embodiment, the device 116 for passing a varying current through the coil 114 is electrically connected between the electrical power source 113 and the coil 114. In this embodiment, the controller 117 also is electrically connected to the electrical power source 113, and is communicatively connected to the device 116 to control the device 116. More specifically, in this embodiment, the controller 117 is for controlling the device 116, so as to control the supply of electrical power from the electrical power source 113 to the coil 114. In this embodiment, the controller 117 comprises an integrated circuit (IC), such as an IC on a printed circuit board (PCB). In other embodiments, the controller 117 may take a different form. In some embodiments, the apparatus 100 may have a single electrical or electronic component comprising the device 116 and the controller 117. The controller 117 is operated in this embodiment by user-operation of the user interface 118. The user interface 118 may comprise a push-button, a toggle switch, a dial, a touchscreen, or the like. In other embodiments, the user interface 118 may be remote and connected to the rest of the apparatus 100 tirelessly, such as via Bluetooth.

In this embodiment, operation of the user interface 118 by a user causes the controller 117 to cause the device 116 to cause an alternating electrical current to pass through the coil 114. This causes the coil 114 to generate an alternating magnetic field. The coil 114 and the heating zone 110 of the apparatus 100 are suitably relatively positioned so that, when the consumable is located in the heating zone 110, the varying magnetic field produced by the coil 114 penetrates heating material of the consumable, such as heating material in the carrier 16 of the consumable. When the heating material is electrically-conductive, this penetration causes the generation of one or more eddy currents in the heating material. The flow of eddy currents in the heating material against the electrical resistance of the heating material causes the heating material to be heated by Joule heating. When the heating material is made of a magnetic material, the orientation of magnetic dipoles in the heating material changes with the changing applied magnetic field, which causes heat to be generated in the heating material.

The apparatus 100 of this embodiment comprises a temperature sensor 119 for sensing a temperature of the heating zone 110. The temperature sensor 119 is communicatively connected to the controller 117, so that the controller 117 is able to monitor the temperature of the heating zone 110. On the basis of one or more signals received from the temperature sensor 119, the controller 117 may cause the device 112 to adjust a characteristic of the varying or alternating electrical current passed through the coil 114 as necessary, in order to ensure that the temperature of the heating zone 110 remains within a predetermined temperature range. The characteristic may be, for example, amplitude or frequency or duty cycle. Within the predetermined temperature range, in use the aerosolizable material 14 within a consumable located in the heating zone 110 is heated sufficiently to volatilize at least one component of the aerosolizable material 14 without combusting the aerosolizable material 14. Accordingly, the controller 1, and the apparatus 100 as a whole, is arranged to heat the aerosolizable material 14 to volatilize the at least one component of the aerosolizable material 14 without combusting the aerosolizable material 14. In some embodiments, the temperature range is about 50° C. to about 350° C., such as between about 100° C. and about 300° C., or between about 120° C. and about 350° C., or between about 140° C. and about 250° C., or between about 200° C. and about 270° C. In other embodiments, the temperature range may be other than one of these ranges. In some embodiments, the upper limit of the temperature range could be greater than 350° C. In some embodiments, the consumable may be non-combustible, for example in these ranges of temperatures. In some embodiments, the temperature sensor 119 may be omitted.

In some embodiments, the device 112 comprises a heatable element 120 comprising heating material, wherein the heatable element 120 is in thermal contact with the heating zone 110, and wherein the magnetic field generator is for generating a varying magnetic field for penetrating the heatable element 120 so as to cause heating of the heatable element 120 and thus the heating zone 110. Such apparatuses 100 are suitable for use when the consumable does not itself comprise heating material for use in heating the aerosolizable material 14. In some embodiments, the heatable element 120 may project into the heating zone 110 so as to be located in the air gap 10 of the consumable when the consumable is in the heating zone 110. In some other embodiments, the heatable element 120 may be located radially outwards of the consumable when the consumable is in the heating zone 110. For example, the heatable element 120 may at least partially define the heating zone 110.

In some cases in use, substantially all of the amorphous solid is less than about 4 mm, 3 mm, 2 mm or 1 mm from the heater (i.e. the heatable element 120 or the resistive heater). In some cases, the solid is disposed between about 0.010 mm and 2.0 mm from the heater, suitably between about 0.02 mm and 1.0 mm, suitably 0.1 mm to 0.5 mm. These minimum distances may, in some cases, reflect the thickness of a carrier that supports the amorphous solid. In some cases, a surface of the amorphous solid may directly abut the heater.

In some embodiments, the device 112 for causing heating of the aerosolizable material when the consumable is in the heating zone 110 is configured for heating different sections of the heating zone 110 independently of each other, such as by way of comprising independently-controllable heatable elements 120.

In some embodiments, the heating material of the consumable 1, 2, 3, 4, 5, or of the heatable element of the apparatus 100, is aluminum. However, in other embodiments, the heating material may comprise one or more materials selected from the group consisting of: an electrically-conductive material, a magnetic material, and a magnetic electrically-conductive material. In some embodiments, the heating material may comprise a metal or a metal alloy. In some embodiments, the heating material may comprise one or more materials selected from the group consisting of: aluminum, gold, iron, nickel, cobalt, conductive carbon, graphite, steel, plain-carbon steel, mild steel, stainless steel, ferritic stainless steel, molybdenum, silicon carbide, copper, and bronze. Other heating material(s) may be used in other embodiments.

In some embodiments, such as those in which the heating material comprises iron, such as steel (e.g. mild steel or stainless steel), or aluminum, the heating material may be coated to help avoid corrosion or oxidation of the heating material in use. Such coating may, for example, comprise nickel plating, gold plating, or a coating of a ceramic or an inert polymer.

In some embodiments, the consumable 1, 2, 3, 4, 5 may comprise heating material that is partially or fully embedded in the aerosolizable material 14. In some embodiments, the aerosolizable material 14 may comprise heating material. In some embodiments, the aerosolizable material 14 may be free from heating material.

In some embodiments, the aerosolizable material comprises tobacco. However, in other embodiments, the aerosolizable material may consist of tobacco, may consist substantially entirely of tobacco, may comprise tobacco and aerosolizable material other than tobacco, may comprise aerosolizable material other than tobacco, or may be free from tobacco. In some embodiments, the aerosolizable material may comprise a vapor or aerosol forming agent or a humectant, such as glycerol, propylene glycol, triacetin, or diethylene glycol.

In some embodiments, the consumable is non-combustible. In some embodiments, the consumable is configured so as not to be combustible in use.

In some embodiments, once all, or substantially all, of the volatilizable component(s) of the aerosolizable material 14 in the consumable 1, 2, 3, 4, 5 has/have been spent, the user may remove the consumable 1, 2, 3, 4, 5 from the heating zone 110 of the apparatus 100 and dispose of the consumable 1, 2, 3, 4, 5. The user may subsequently re-use the apparatus 100 with another of the consumables 1, 2, 3, 4, 5. However, in other respective embodiments, the apparatus 100 and the consumable 1, 2, 3, 4, 5 may be disposed of together once the volatilizable component(s) of the aerosolizable material 14 has/have been spent.

In some embodiments, the consumable 1, 2, 3, 4, 5 is sold, supplied or otherwise provided separately from the apparatus 100 with which the consumable 1, 2, 3, 4, 5 is usable. However, in some embodiments, the apparatus 100 and one or more of the consumables 1, 2, 3, 4, 5 may be provided together as a system, such as a kit or an assembly, possibly with additional components, such as cleaning utensils.

For the avoidance of doubt, where in this specification the term "comprises" is used in defining the invention or features of the invention, embodiments are also disclosed in which the invention or feature can be defined using the terms "consists essentially of" or "consists of" in place of "comprises". Reference to a material "comprising" certain features means that those features are included in, contained in, or held within the material.

In order to address various issues and advance the art, the entirety of this disclosure shows by way of illustration and example various embodiments in which the claimed invention may be practiced and which provide for superior consumables for use with apparatus for heating aerosolizable material to volatilize at least one component of the aerosolizable material, methods of manufacturing a consumable for use with apparatus for heating aerosolizable material to volatilize at least one component of the aerosolizable material, and systems comprising such a consumable and such apparatus. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A consumable for use with an apparatus for heating aerosolizable material to volatilize at least one component of the aerosolizable material, wherein the consumable comprises:

a hollow tube comprising a carrier, the aerosolizable material, a body of porous aerosol containment material and an outer cover, wherein the aerosolizable material comprises an amorphous solid coated on the carrier, wherein the body of porous aerosol containment material is configured to contain aerosol generated from the aerosolizable material during heating of the aerosolizable material in use, wherein the body of porous aerosol containment material is located between the outer cover and the aerosolizable material, and wherein the carrier has one or more holes extending therethrough for permitting the aerosol generated from the aerosolizable material during heating of the aerosolizable material in use to pass to a surface of the consumable.

2. The consumable of claim 1, wherein at least part of the carrier is located radially inwards of the aerosolizable material.

3. The consumable of claim 1, wherein the carrier forms at least part of a surface of the hollow tube.

4. The consumable of claim 3, wherein the surface of the hollow tube is an innermost surface of the hollow tube.

5. The consumable of claim 1, wherein the amorphous solid is affixed to the carrier, and wherein the carrier forms at least part of an innermost surface of the hollow tube.

6. The consumable of claim 1, wherein the carrier is tubular.

7. The consumable of claim 1, wherein the aerosolizable material is tubular.

8. The consumable of claim 1, further comprising a heating material that is heatable by penetration with a varying magnetic field to thereby heat the aerosolizable material.

9. The consumable of claim 8, wherein the heating material comprises one or more materials selected from the group consisting of an electrically-conductive material, a magnetic material, and a magnetic electrically-conductive material.

10. The consumable of claim 8, wherein the heating material comprises a metal or a metal alloy.

11. The consumable of claim 8, wherein the heating material comprises one or more materials selected from the group consisting of aluminum, gold, iron, nickel, cobalt, conductive carbon, graphite, steel, plain-carbon steel, mild steel, stainless steel, ferritic stainless steel, molybdenum, silicon carbide, copper, and bronze.

12. The consumable of claim 8, wherein the carrier comprises the heating material.

13. The consumable of claim 12, wherein the carrier comprises a closed circuit of the heating material, wherein the closed circuit is closed about the hollow tube.

14. The consumable of claim 8, wherein the carrier comprises a first layer and a second layer, wherein the first layer comprises the heating material, wherein the second layer is not heatable by penetration with the varying magnetic field, and wherein the first layer is located between the aerosolizable material and the second layer.

15. The consumable of claim 1, wherein the carrier forms at least part of the surface of the consumable.

16. The consumable of claim 1, wherein the aerosolizable material is located radially between the carrier and the body of porous aerosol containment material.

17. The consumable of claim 1, wherein the aerosolizable material has a thickness in a direction perpendicular to an axial direction of the consumable of between about 0.1 millimeters and about 5 millimeters.

18. The consumable of claim 1, wherein the amorphous solid has a tensile strength of from 200 N/m to 900 N/m.

19. The consumable of claim 1, wherein the amorphous solid has a density of 30 g/m$^2$ to 120 g/m$^2$.

* * * * *